United States Patent [19]
Rosen

[11] Patent Number: 5,499,974
[45] Date of Patent: Mar. 19, 1996

[54] EXTERNAL PUMP STROKE INDICATOR FOR USE WITH AN IMPLANTED MEDICATION INFUSION SYSTEM

[75] Inventor: Jan Rosen, Grillby, Sweden

[73] Assignee: Siemens Elema AB, Solna, Sweden

[21] Appl. No.: 326,209

[22] Filed: Oct. 20, 1994

[30] Foreign Application Priority Data

Oct. 22, 1993 [SE] Sweden .................................. 9303485

[51] Int. Cl.$^6$ .................................................. A61M 5/48
[52] U.S. Cl. .......................................... 604/118; 604/254
[58] Field of Search .................................. 604/118, 254, 604/141

[56] References Cited

U.S. PATENT DOCUMENTS

| | | | |
|---|---|---|---|
| 3,101,710 | 8/1963 | Koehn | 604/254 |
| 3,465,784 | 9/1969 | Cofoid | 604/254 |
| 3,669,094 | 6/1972 | Heyer | 604/118 |
| 3,980,082 | 9/1976 | Miller | 604/118 |
| 4,055,176 | 10/1977 | Lundquist | 604/254 |
| 4,626,243 | 12/1986 | Singh et al. | 604/141 |
| 4,801,293 | 1/1989 | Jackson | 604/118 |
| 5,197,322 | 3/1993 | Indravudh | 604/141 |
| 5,346,477 | 9/1994 | Edwards | 604/118 |

FOREIGN PATENT DOCUMENTS 0410734  1/1991  European Pat. Off. .

*Primary Examiner*—Paul J. Hirsch
*Attorney, Agent, or Firm*—Hill, Steadman & Simpson

[57] ABSTRACT

The invention is directed to an external pump stroke indicator for use with in an implanted medication infusion system of the type having a pump for conveying medication into the patient, an opening covered by a septum is arranged at the output of the pump. The indicator includes a cylinder composed of a transparent material and connectable via its lower end to the opening in an essentially upright attitude, the cylinder being filled with a liquid. A movable sinker member is provided in the cylinder, the movable sinker member normally resting as a result of its weight against a seat provided in the cylinder that limits the motion of the sinker member in the direction of the lower end of the cylinder. The sinker member is composed of a material that has a higher density than that of the liquid, so that the sinker member normally rests against the seat and only moves when pressure elevations that are generated by the pump strokes of the infusion system arise in the liquid.

11 Claims, 1 Drawing Sheet

EXTERNAL PUMP STROKE INDICATOR FOR USE WITH AN IMPLANTED MEDICATION INFUSION SYSTEM

BACKGROUND OF THE INVENTION

1. Field of the Invention

The present invention is directed to an external pump stroke indicator for use in an implanted medication infusion system of the type having a pump for conveying the medication into the patient, with an opening covered by a septum is arranged at the output of the pump.

2. Description of the Prior Art

Openings (ports) in implanted infusion systems are normally covered by a septum as well as by skin and a fatty layer of the patient. Connection of external equipment normally ensues with the assistance of a cannula that is conducted through the skin and the fat of the patient as well as through said septum. It is important that the cannula be introduced into the opening in a correct way. If the cannula is not introduced to a sufficient extent, i.e. the tip remains in the septum after penetrating the skin and the fat, no connection between the opening and the external equipment is achieved. If the external equipment is, for example, a device for measuring the flow resistance in an implanted catheter according to U.S. application having Attorney Docket No. P94,2608 corresponding to Swedish Patent Application 930 3484-1, filed simultaneously herewith, an inadequate introduction of the cannula leads to a faulty detection of a blockage in the catheter.

When, by contrast, the cannula is introduced too far into the opening, there is a risk that the tip will be destroyed and the destroyed tip will subsequently tear the septum when the cannula is withdrawn, an explantation of the infusion system thus becoming necessary.

The position of the cannula in the opening cannot be optically observed. A display or some other kind of acknowledgement that the cannula has been correctly introduced into the opening is therefore desirable. A commercially obtainable pressure transducer of the type which is used once and then is disposed of for these purposes in certain instances.

SUMMARY OF THE INVENTION

It is an object of the present invention to provide a new type of such a display device having a structure which is extremely simple and disposable for employment in combination with sterile systems and which reliably indicates when the cannula has been correctly introduced into the opening of an implanted infusion system.

The above object is achieved in accordance with the principles of the present invention in a pump stroke indicator for use with an implanted medication infusion system, the infusion system including a pump for conveying the medication to the patient and having an opening covered by a septum disposed at an output of the pump, the indicator including a cylinder composed of a transparent material connected to the aforementioned opening at a lower end of the cylinder so that the cylinder is in a substantially upright orientation. The cylinder is filled with liquid and contains a sinker member movable in the liquid in the cylinder. The sinker member normally rests, as a consequence of its weight, against a seat disposed in the cylinder which limits the motion of the sinker member in a direction toward the lower end of the cylinder. The sinker member is composed of material having a higher density than the density of the liquid, so that the sinker member normally rests against the seat, and only moves away from the seat when pressure elevations in the liquid occur which are produced by the pump strokes of the infusion system.

The sinker member is composed of a material that is adequately heavy for the sinker member normally to sink down to a seat provided in the cylinder. The seat limits the movement of the sinker member in the direction of the end of the cylinder that is provided for connection to the opening, whereby the sinker member moves only given pressure elevations that are produced by the pump strokes of the infusion system. The sinker member should not react to slow variations in the flow of the liquid employed, for example when the patient breaths, i.e. the sinker member should not move as a result of pressure differences between the abdominal cavity and its surroundings but should only move as a consequence of pump strokes of the pump of the infusion system. When the pump stroke indicator is correctly connected to the opening, so that a free connection has been produced, each pump stroke produces a pressure pulse having an excess pressure of preferably 0.5 bar that lifts the sinker member. When the indicator is connected to the opening in the correct way, for example via a cannula, direct observation of the sinker member attached in the transparent cylinder shows that this sinker member lifts at every pump stroke when a free connection to the opening has been produced. A slow introduction of the cannula while the operator is viewing the indicator can avoid the cannula reaching the base of the pump and thereby being damaged.

In an embodiment of the indicator of the invention a sterile filter for avoiding excess pressures is arranged at the upper end of the cylinder. The penetration of microorganisms is also prevented by the filter.

DESCRIPTION OF THE PREFERRED EMBODIMENTS

Figure 1:
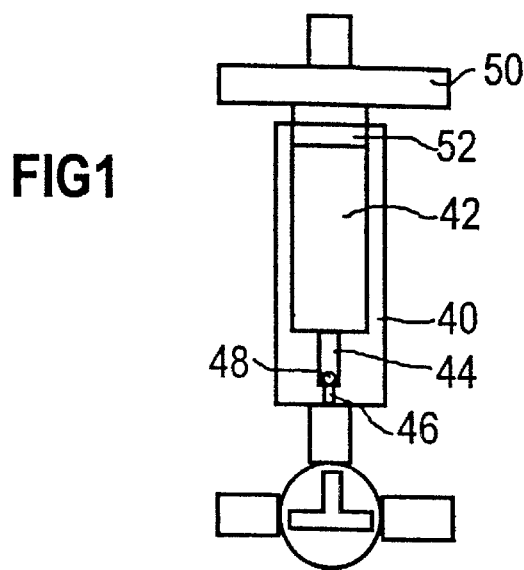
FIG. 1 illustrates an external pump stroke indicator of the invention.

The pump indicator of the invention shown in FIG. 1 has a body 40 composed of a transparent material such as, for example, a transparent polymer in which a cylinder having three sections 42, 44 and 46 with different diameters is arranged. The section 46 preferably has a diameter in the range of 0.7–0.8 mm, the section 44 preferably has a diameter of approximately 1.2 mm and the section 42 preferably has a diameter that far exceeds 1 mm.

A sinker member in the form of a ball 48 is arranged in the middle section 44. The ball 48 can have a diameter of approximately 1 mm.

Figure 2:
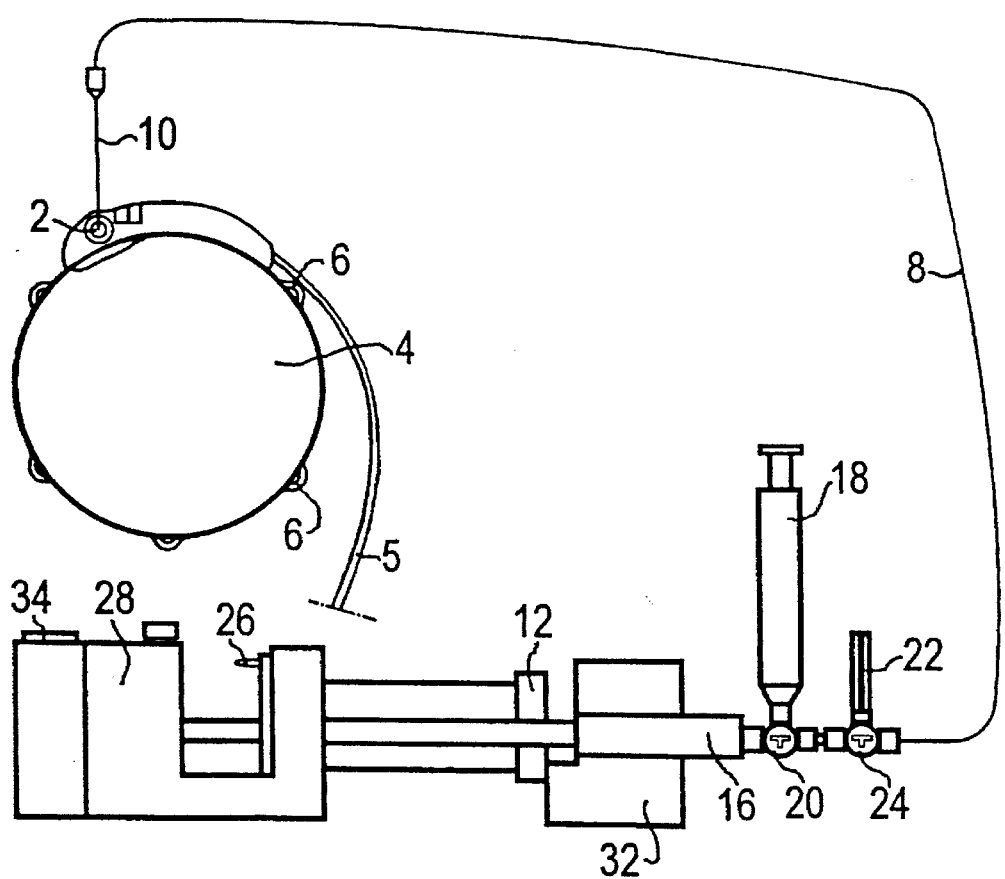
FIG. 2 shows the employment of an indicator of the invention in conjunction with a device for measuring the flow resistance of a catheter in an implanted infusion system.

For example, the cylinder formed by sections 42, 44 and 46 is connected to luer couplings via a three-way cock 24 and is connected to the rinsing input 2 of an implanted infusion system or infusion device via suitable connector elements 8 and 10 that are shown in FIG. 2.

A preferably hydrophobic, sterile filter 50, of preferably 0.2 μm in thickness, is arranged at the upper end of the cylinder formed by sections 42, 44 and 46. Care is exercised when filling the cylinder that an air gap 52 is present between the upper surface of the liquid and the filter, this air gap 52 assuring that the filter is not moistened by the liquid since it can otherwise cease functioning. The excess air present in the indicator and in the connections thereof is emptied through the filter 50.

In order to explain the operation of the external pump stroke indicator of the invention in greater detail, the employment of the indicator for measuring a flow resistance of a catheter in an implanted infusion system for medications shall be described in conjunction with FIG. 2, this implanted infusion system being of a type disclosed in the aforementioned co-pending U.S. application having Attorney Docket No. P94,2608.

FIG. 2 shows an implantable infusion system or infusion device 4 having a catheter 5 and a rinsing input 2 that are connected to a measuring device of the invention. It is shown in FIG. 2 that elements for a subcutaneous fastening after implantations are provided at the housing of the infusion device 4.

The device for measuring the flow resistance in a catheter 5 is connected via a connecting line 8 and a cannula 10 to the rinsing input 2 of the infusion device 4, whereby the cannula 10 is to be introduced into the rinsing input 2 through the skin and through potential fatty layers as well as through the rubber septum that covers the rinsing input 2.

The measuring instrument is a testing device having a spring-controlled piston 12. A disposable syringe 16 is secured to one end thereof. The syringe 16 preferably has a volume of 2 ml and can be filled with a liquid, for example an "insulin dilution buffer" that is harmless to the patient.

A 10 ml syringe 18 is connected to the output of the testing device via a three-way coupling 20. This syringe 18 is filled with the liquid being employed and serves as a reservoir. The syringe 16 is consequently filled by the syringe 18 before the measuring procedure. The syringe 18 can also be employed for rinsing the implanted catheter 5 clean after the implementation of the measuring procedure.

An external pump stroke indicator 22 of FIG. 1 is also connected via a further three-way valve 24. The cylinder formed by sections 42, 44 and 46 of the indicator 22 is also filled to a desired level with the syringe 18.

The weight of the ball 48 is such that it does not float at the surface of the liquid but sinks in the direction of the seat, i.e. in the region of the transition between the sections 44 and 46. The ball 48 thus consists of an adequately heavy material such as, for example, stainless steel or a ceramic, preferably sapphire, so that it does not react to slow variations in the liquid flow, for example given respiration of the patient, i.e. such that the ball should not move as a result of pressure differences between the abdominal cavity and the environment thereof. When the cannula 10 has been correctly introduced into the rinsing input 2, each pump stroke of the infusion device 4 will generate a pressure pulse in the liquid that lifts the ball 48. This movement of the ball 48 thus represents an acknowledgement that the cannula 10 has been correctly introduced into the rinsing input 2, whereby the operator can observe the movement of the ball 48 through the transparent cylinder 4.

Although modifications and changes may be suggested by those skilled in the art, it is the intention of the inventor to embody within the patent warranted hereon all changes and modifications as reasonably and properly come within the scope of his contribution to the art.

I claim as my invention:

1. A pump stroke indicator for use with an implanted medication infusion system, said implanted medication infusion system including a pump for conveying medication in vivo to a patient in whom the system is implanted, and said pump having an opening covered by a septum disposed at an output of said pump, said pump stroke indicator comprising:

a cylinder composed of a transparent material, said cylinder having a lower end;

means for transcutaneously placing said cylinder in fluid communication with said opening in said pump with said cylinder oriented in a substantially upright attitude;

a liquid contained in said cylinder, said liquid having a density;

a seat disposed in said cylinder; and a sinker member disposed above said seat in said cylinder and movable in said liquid in said cylinder, said sinker member having a density which is greater than the density of said liquid so that said sinker member normally rests as a consequence of its weight on said seat and being displaced from said seat due to pressure elevations in said liquid occurring due to pump strokes of said pump in said implanted medication infusion system.

2. A pump stroke indicator as claimed in claim 1 wherein said cylinder comprises three connected sections arranged in a sequence from said lower end of said cylinder and including a lower section at said lower end, a middle section and an upper section, said sections having successively increasing respective diameters with said lower section having a smallest diameter, said sinker member being disposed within said middle section, and said lower section and said middle section having a transition region forming said seat.

3. A pump stroke indicator as claimed in claim 1 wherein said cylinder is composed of a transparent polymer body.

4. A pump stroke indicator as claimed in claim 1 wherein said sinker member is a ball.

5. A pump stroke indicator as claimed in claim 1 wherein said sinker member is composed of stainless steel.

6. A pump stroke indicator as claimed in claim 1 wherein said sinker member is composed of a ceramic.

7. A pump stroke indicator as claimed in claim 1 wherein said sinker member is composed of sapphire.

8. A pump stroke indicator as claimed in claim 1 wherein said cylinder has an upper end disposed opposite said lower end, and wherein said cylinder is fillable with said liquid at said upper end of said cylinder.

9. A pump stroke indicator as claimed in claim 8 further comprising a sterile filter disposed at said upper end of said cylinder.

10. A pump stroke indicator as claimed in claim 1 wherein said means for transcutaneously placing said cylinder in fluid communication with said opening in said pump comprises a cannula introducible through the skin of said patient and through said septum of said pump, and a fluid conduit connecting said cannula and said cylinder.

11. A pump stroke indicator as claimed in claim 10 wherein said implanted medication infusion system further includes a catheter for delivering said medication to a specified site in said patient, and wherein said pump stroke indicator further comprises testing means for measuring flow resistance in said catheter and a three-way valve connecting said testing means, said fluid conduit and said cylinder.

* * * * *